United States Patent
Gallagher et al.

(10) Patent No.: US 10,568,578 B2
(45) Date of Patent: Feb. 25, 2020

(54) MULTI-SOURCE DOPPLER RADAR SYSTEM FOR MONITORING CARDIAC AND RESPIRATORY FUNCTIONS AND POSITIONING OF VEHICLE SEAT OCCUPANT

(71) Applicant: Lear Corporation, Southfield, MI (US)

(72) Inventors: David Gallagher, Sterling Heights, MI (US); Francesco Migneco, Salene, MI (US)

(73) Assignee: Lear Corporation, Southfield, MI (US)

( * ) Notice: Subject to any disclaimer, the term of this patent is extended or adjusted under 35 U.S.C. 154(b) by 232 days.

(21) Appl. No.: 15/887,161

(22) Filed: Feb. 2, 2018

(65) Prior Publication Data
US 2019/0239815 A1   Aug. 8, 2019

(51) Int. Cl.
| | |
|---|---|
| *A61B 5/00* | (2006.01) |
| *G01S 13/06* | (2006.01) |
| *G01S 7/41* | (2006.01) |
| *G01S 13/50* | (2006.01) |
| *G01S 13/87* | (2006.01) |
| *G01S 13/88* | (2006.01) |
| *B60N 2/90* | (2018.01) |

(Continued)

(52) U.S. Cl.
CPC .......... *A61B 5/6893* (2013.01); *A61B 5/0205* (2013.01); *B60N 2/90* (2018.02); *G01S 7/414* (2013.01); *G01S 7/415* (2013.01); *G01S 13/06* (2013.01); *G01S 13/50* (2013.01); *G01S 13/87* (2013.01); *G01S 13/88* (2013.01); *A61B 5/024* (2013.01); *A61B 5/0507* (2013.01); *A61B 5/08* (2013.01); *A61B 2562/04* (2013.01); *G01S 2013/0272* (2013.01)

(58) Field of Classification Search
CPC ......... A61B 5/00; A61B 5/0205; A61B 5/024; A61B 5/08; G01S 7/414; G01S 7/415; G01S 13/06; B60N 2/90
USPC ........................................................ 701/36
See application file for complete search history.

(56) References Cited

U.S. PATENT DOCUMENTS

| | | |
|---|---|---|
| 6,753,780 B2 | 6/2004 | Li |
| 8,725,311 B1 | 5/2014 | Breed |

(Continued)

OTHER PUBLICATIONS

Changzhi Li and Jenshan Lin, Random Body Movement Cancellation in Doppler Radar Vital Sign Detection, IEEE Transactions on Microwave Theory and Techniques, vol. 56, No. 12, Dec. 2008.

*Primary Examiner* — Tan Q Nguyen
(74) *Attorney, Agent, or Firm* — Brooks Kushman P.C.

(57) ABSTRACT

A seating system for a vehicle includes a vehicle seat, a first Doppler radar sensor positioned within the seatback and aligned with the heart of a person sitting in the seat, a second Doppler radar sensor positioned within the seatback and offset from alignment with the heart, and a controller. The first sensor transmits a signal toward the heart and receives a first reflected signal as modulated by heart movement and by a random motion of the person. The second sensor transmits a signal toward an anatomical location of the person offset from the heart and receives a second reflected signal as modulated by the random motion of the person. The controller generates a biometric signal corresponding to the heart movement, without random motion artifacts, based on a difference between the reflected signals whereby the biometric signal is indicative of cardiac information of the person.

16 Claims, 4 Drawing Sheets

(51) Int. Cl.
*A61B 5/0205* (2006.01)
*A61B 5/024* (2006.01)
*A61B 5/05* (2006.01)
*A61B 5/08* (2006.01)
*G01S 13/02* (2006.01)

(56) References Cited

U.S. PATENT DOCUMENTS

| | | |
|---|---|---|
| 8,834,364 B2 | 9/2014 | Heneghan et al. |
| 9,229,905 B1 | 1/2016 | Penilla et al. |
| 9,492,099 B2 | 11/2016 | Gamble et al. |
| 10,390,748 B2 * | 8/2019 | Lee ...................... A61B 5/4812 |
| 2009/0209829 A1 * | 8/2009 | Yanagidaira ........... A61B 5/165 |
| | | 600/301 |
| 2010/0222687 A1 | 9/2010 | Thijs et al. |
| 2012/0010514 A1 * | 1/2012 | Vrazic .................. A61B 5/0205 |
| | | 600/484 |
| 2013/0030256 A1 * | 1/2013 | Fujita ....................... A61B 5/18 |
| | | 600/300 |
| 2015/0196209 A1 * | 7/2015 | Morris ................... G16H 40/67 |
| | | 600/480 |
| 2016/0236690 A1 * | 8/2016 | Juneja ....................... G06F 3/16 |
| 2018/0348759 A1 * | 12/2018 | Freeman .............. G05D 1/0061 |

* cited by examiner

MULTI-SOURCE DOPPLER RADAR SYSTEM FOR MONITORING CARDIAC AND RESPIRATORY FUNCTIONS AND POSITIONING OF VEHICLE SEAT OCCUPANT

TECHNICAL FIELD

The present invention relates to Doppler radar systems for sensing cardiac (e.g., heart) and respiratory (e.g., breathing) functions of a person occupying a vehicle seat and for sensing positioning of the person in the vehicle seat.

BACKGROUND

Approaches to monitor the physiological state of a person include attaching adhesive electrodes to the skin of the person. These approaches are cumbersome and are not suitable for use with vehicular applications involving a person sitting in a vehicle seat of an operating vehicle.

SUMMARY

In an embodiment, a seating system for a vehicle includes a vehicle seat, a first Doppler radar sensor, a second Doppler radar sensor, and a controller. The seat includes a seatback. The first sensor is positioned at a first location within the seatback corresponding to an anatomical location of the heart of a person sitting in the seat. The second sensor is positioned at a second location within the seatback corresponding to an anatomical location of the person offset from the heart of the person.

The first sensor is configured to transmit a first signal from behind the person toward the anatomical location of the heart of the person. The first sensor is further configured to receive a first reflected signal of the first signal reflected from the person as modulated by a movement of the heart of the person and by a random motion of the person. The first reflected signal includes a component corresponding to the heart movement and a component corresponding to the random motion of the person.

The second sensor is configured to transmit a second signal from behind the person toward the anatomical location of the person offset from the heart of the person. The second sensor is further configured to receive a second reflected signal of the second signal reflected from the person as modulated by the random motion of the person. The second reflected signal includes the component corresponding to the random motion of the person.

The controller is configured to remove the second reflected signal from the first reflected signal to generate a biometric signal having the component corresponding to the heart movement and being void of the component corresponding to the random motion of the person whereby the biometric signal is indicative of cardiac information of the person.

In an embodiment, a seating system for a vehicle includes a vehicle seat, a first Doppler radar sensor, a second Doppler radar sensor, and a controller. The seat includes a seatback. The first sensor is positioned at a location within the seatback corresponding to an anatomical location of the heart of a person sitting in the seat. The second sensor is positioned in front of the person at a location within the vehicle corresponding to the anatomical location of the heart of the person.

The first sensor is configured to transmit a first signal from behind the person toward the anatomical location of the heart of the person. The first sensor is further configured to receive a first reflected signal of the first signal reflected from the person as modulated by a movement of the heart of the person and by a random motion of the person relative to the location of the first sensor. The first reflected signal includes a component corresponding to the movement of the heart of the person and a component corresponding to the random motion of the person relative to the location of the first sensor.

The second sensor is configured to transmit a second signal from in front of the person toward the anatomical location of the heart of the person. The second sensor is further configured to receive a second reflected signal of the second signal reflected from the person as modulated by the movement of the heart of the person and by the random motion of the person relative to the location of the second sensor. The second reflected signal includes the component corresponding to the movement of the heart of the person and a component corresponding to the random motion of the person relative to the location of the second sensor.

The component of the first reflected signal corresponding to the random motion of the person relative to the location of the first sensor and the component of the second reflected signal corresponding to the random motion of the person relative to the location of the second sensor are additive inverses of one another.

The controller is configured to combine the first and second reflected signals to generate a biometric signal having the component corresponding to the movement of the heart of the person and being void of the components corresponding to the random motion of the person relative to the locations of the first and second sensors whereby the biometric signal is indicative of cardiac information of the person.

In an embodiment, a seating system for a vehicle includes a vehicle seat, a first Doppler radar sensor, a second Doppler radar sensor, and a controller. The seat includes a seatback and a seat bottom. The first sensor is positioned at a location within the seatback corresponding to an anatomical location of the heart of a person sitting in the seat. The second sensor is positioned at a location within the seat bottom corresponding to the anatomical location of the heart of the person.

The first sensor is configured to transmit a first signal from behind the person toward the anatomical location of the heart of the person. The first sensor is further configured to receive a first reflected signal of the first signal reflected from the person as modulated by a movement of the heart of the person relative to the location of the first sensor. The first reflected signal includes a first component corresponding to the movement of the heart of the person relative to the location of the first sensor.

The second sensor is configured to transmit a second signal from beneath the person toward the anatomical location of the heart of the person. The second sensor is further configured to receive a second reflected signal of the second signal reflected from the person as modulated by the movement of the heart of the person relative to the location of the second sensor. The second reflected signal includes a second component corresponding to the movement of the heart of the person relative to the location of the second sensor.

The controller is configured to process the first and second reflected signals to extract the first component from the first reflected signal based on a correlation with the second component of the second reflected signal. The controller is further configured to generate a biometric signal having the first component whereby the biometric signal is indicative of cardiac information of the person.

In embodiments, a seating system may further include a third sensor positioned at a third location within the seatback corresponding to an anatomical location of a left side of a torso of the person and a fourth sensor positioned at a fourth location within the seatback corresponding to an anatomical location of a right side of the torso. The third sensor is configured to transmit a third signal from behind the person toward the anatomical location of the left side of the torso and to receive a third reflected signal of the third signal reflected from the person as modulated by rotation movement of the torso. The third reflected signal includes a component corresponding to the rotation movement of the torso relative to the third location of the third sensor. The fourth sensor is configured to transmit a fourth signal from behind the person toward the anatomical location of the right side of the torso and to receive a fourth reflected signal of the fourth signal reflected from the person as modulated by rotation movement of the torso. The fourth reflected signal includes a component corresponding to the rotation movement of the torso relative to the fourth location of the fourth sensor. The controller is further configured to generate a position signal indicative of positioning information of the person based on a comparison of the third and fourth reflected signals.

In other embodiments, a seating system may further include a third sensor positioned at a third location within the seatback corresponding to an anatomical location of a left lung of the person and a fourth sensor positioned at a fourth location within the seatback corresponding to an anatomical location of a right lung of the person. The third sensor is configured to transmit a third signal from behind the person toward the anatomical location of the left lung and to receive a third reflected signal of the third signal reflected from the person as modulated by movement of the left lung. The third reflected signal includes a component corresponding to the movement of the left lung. The fourth sensor is configured to transmit a fourth signal from behind the person toward the anatomical location of the right lung and to receive a fourth reflected signal of the fourth signal reflected from the person as modulated by movement of the right lung. The fourth reflected signal includes a component corresponding to the movement of the right lung. The controller is further configured to generate a lung status signal indicative of respiratory information of the person based on a comparison of the third and fourth reflected signals.

DETAILED DESCRIPTION

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
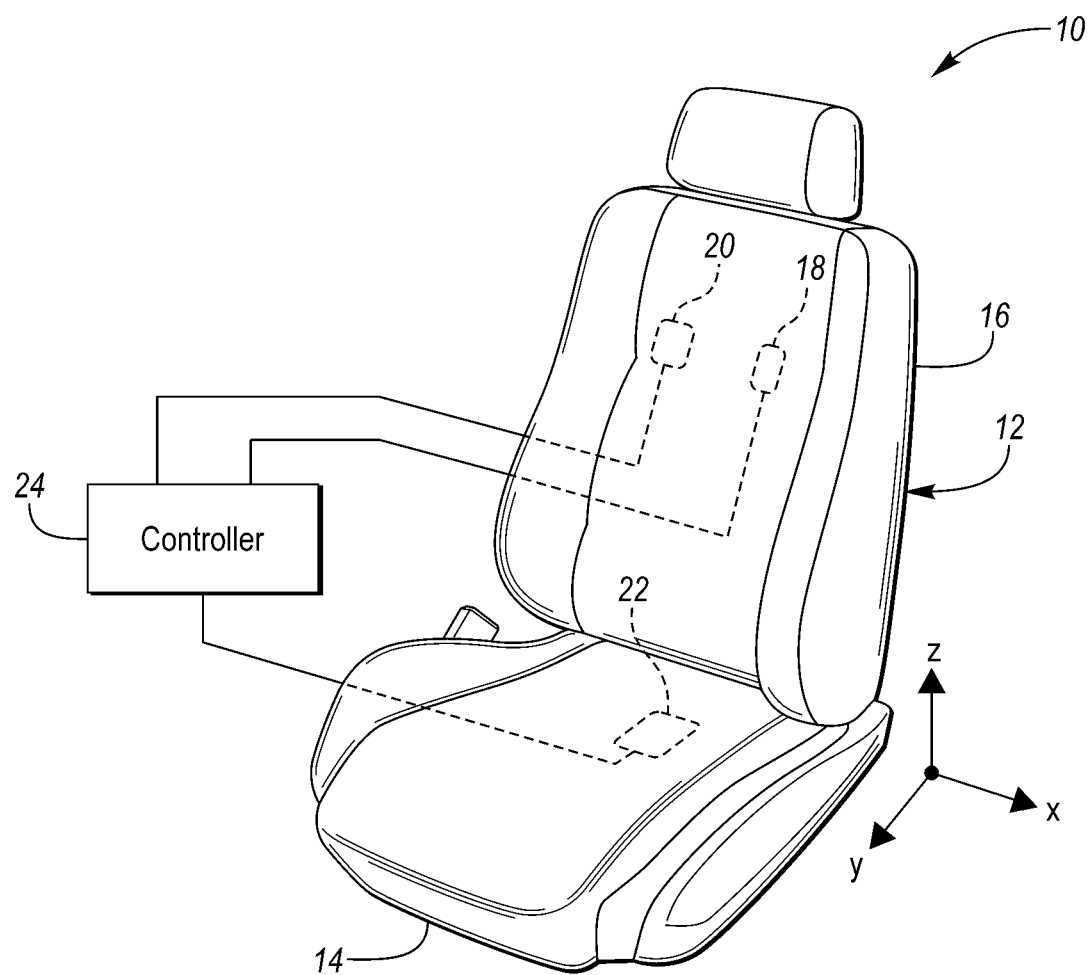
FIG. 1 illustrates a perspective view of a seating system for a vehicle including a perspective view of a vehicle seat of the seating system and a block diagram of other components of the seating system.

Referring now to FIG. 1, a vehicle seating system 10 will be described. Seating system 10 is implemented in a vehicle (not shown). The vehicle may be an automobile, a car, a truck, a boat, an airplane, or the like. Seating system 10 includes a seat 12. A perspective view of seat 12 is shown in FIG. 1. Seat 12 includes a seat bottom (i.e., a seat cushion) 14 and a seatback 16. Seat bottom 14 is configured to support the sitting region of a person sitting in seat 12. As such, seat bottom 14 is beneath a person sitting in seat 12. Seatback 16 is configured to support the back of the person sitting in seat 12. As such, seatback 16 is behind a person sitting in seat 12.

As shown in phantom in FIG. 1, seat 12 includes an array of Doppler radar sensors 18, 20, and 22. First Doppler radar sensor ("first sensor") 18 is located at a first location within seatback 16. The first location within seatback 16 is aligned with an anatomical location of the heart of a person sitting in seat 12. Thus, first sensor 18 is positioned at a first location within seatback 16 corresponding to the anatomical location of the heart of the person.

Second Doppler radar sensor ("second sensor") 20 is located at a second location within seatback 16. The second location within seatback 16 is offset from alignment with the anatomical location of the heart of the person sitting in seat 12. For instance, as indicated in FIG. 1, the second location of second sensor 20 is offset in the x direction from the first location of first sensor 18. Thus, second sensor 20 is positioned at a second location within seatback 16 corresponding to an anatomical location of the person sitting in seat 12 offset from the heart of the person.

Third Doppler radar sensor ("third sensor") 22 is located at a third location within seat bottom 14. The third location within seat bottom 14 is aligned with the anatomical location of the heart of the person sitting in seat 12. Thus, third sensor 22 is positioned at a third location within seat bottom 14 corresponding to the anatomical location of the heart of the person.

As indicated in FIG. 1, first sensor 18 and the anatomical location of the heart of the person sitting in seat 12 aligned with the first sensor are in an x-y plane. Second sensor 20 and the anatomical location of the person sitting in seat 12 offset from the anatomical location of the heart of the person are in the in same x-y plane. Third sensor 22 and the anatomical location of the heart of the person sitting in seat 12 aligned with the third sensor are in a y-z plane.

First sensor 18 is configured to wirelessly transmit a first signal from the first location within seatback 16 behind the person sitting in seat 12 toward the anatomical location of the heart of the person. Upon the first signal illuminating the anatomical location of the heart of the person, the first signal reflects from the person. The first signal reflected from the person is modulated by a movement of the heart of the person and by a random motion of the person. First sensor 18 is further configured to wirelessly receive a first reflected signal of the first signal reflected from the person as modulated by the movement of the heart of the person (e.g., pulsation of arteries of the person's heart) and by the random motion of the person.

Second sensor 20 is configured to wirelessly transmit a second signal from the second location within seatback 16 behind the person sitting in seat 12 toward an anatomical location of the person offset from the heart of the person. Upon the second signal illuminating the anatomical location of the person offset from the heart of the person, the second signal reflects from the person. The second signal reflected from the person is modulated by the random motion of the person. Second sensor 20 is further configured to wirelessly receive a second reflected signal of the second signal reflected from the person as modulated by the random motion of the person.

Third sensor 22 is configured to wirelessly transmit a third signal from the third location within seat bottom 14 beneath the person sitting in seat 12 toward the anatomical location of the heart of the person. Upon the third signal illuminating the anatomical location of the heart of the person, the third signal reflects from the person. The third signal reflected from the person is modulated by the movement of the heart of the person. Third sensor 22 is further configured to wirelessly receive a third reflected signal of the third signal reflected from the person as modulated by the movement of the heart of the person.

Seating system 10 further includes an electronic controller 24. Controller 24 is individually connected to first, second, and third sensors 18, 20, and 22. Controller 24 is configured to individually control sensors 18, 20, and 22 to cause the sensors to wirelessly transmit the first, second, and third signals. Controller 24 is further configured to receive from sensors 18, 20, and 22 the first, second, and third reflected signals wirelessly received by the sensors. As described in greater detail below, controller 24 is further configured to process the first, second, third, and/or other reflected signals to generate biometric signals indicative of cardiac information of the person sitting in seat 12.

Figure 2:
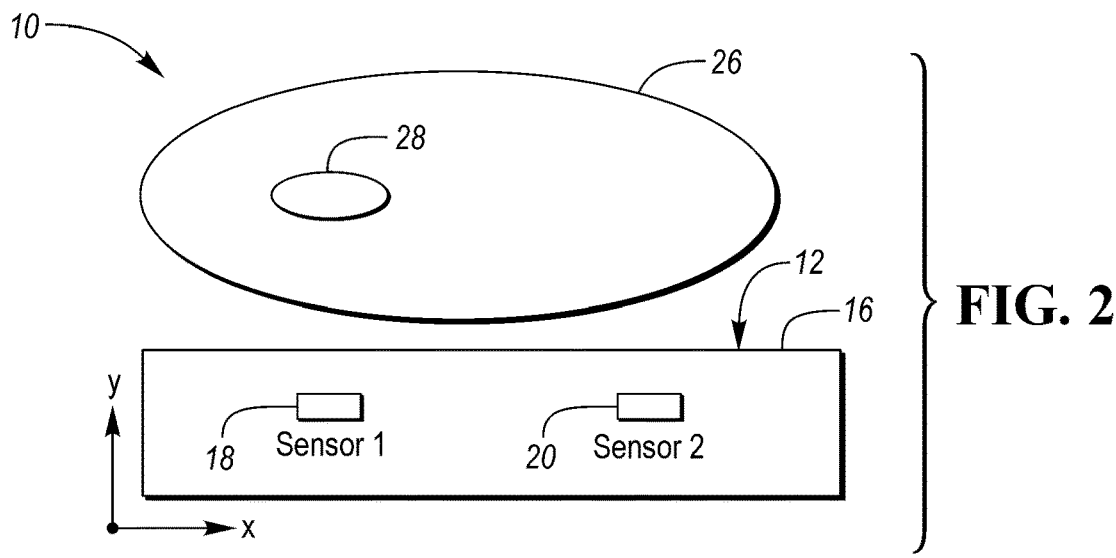
FIG. 2 illustrates a schematic diagram of the seating system according to a first embodiment.

Referring now to FIG. 2, with continual reference to FIG. 1, a schematic diagram of seating system 10 according to a first embodiment is shown. Seating system 10 according to the first embodiment includes first and second sensors 18 and 20. The schematic diagram shown in FIG. 2 is a sectional view of the x-y plane containing first and second sensors 18 and 20. Torso 26 of the person sitting in seat 12 and heart 28 of the person are illustrated per the sectional view.

As shown in FIG. 2, and with reference to FIG. 1, first sensor 18 is aligned with the anatomical location of heart 28 of the person. That is, first sensor 18 (i.e., the biased sensor) is biased towards the anatomical location of heart 28 of the person. Second sensor 20 is aligned with an anatomical location of the person offset in the x direction with the anatomical location of heart 28 of the person.

In operation, controller 24 controls first sensor 18 to wirelessly transmit the first signal toward the anatomical location of heart 28 of the person (e.g., at least toward an anatomically biased location relative to heart 28 of the person). The first signal reflects from the person. The reflected first signal is modulated by the movement of heart 28 of the person, the movement of torso 26 of the person due to breathing of the lungs of the person (i.e., breathing movement, respiratory activity of the person, etc.), and by random motion of the person. The random motion of the person includes movement of torso 26 of the person caused by the person's body unintentionally moving and bouncing around in seat 12 due to vehicle operation. The random motion of the person is a motion artifact akin to noise.

A portion of the reflected first signal reflects towards first sensor 18. This portion of the reflected first signal is a first reflected signal wirelessly received by first sensor 18. As such, the first reflected signal is of the first signal reflected from the person as modulated by the heart movement, the breathing movement, and the random motion of the person. The first reflected signal thereby includes a component corresponding to the heart movement, a component corresponding to the breathing movement, and a component corresponding to the random motion of the person. Controller 24 communicates with first sensor 18 to receive the first reflected signal.

Controller 24 controls second sensor 20 to wirelessly transmit the second signal toward the anatomical location of the person offset from heart 28 of the person. The first and second signals may be the same type of signal concurrently transmitted from the first and second sensors separately. The second signal reflects from the person. The reflected second signal is modulated by the movement of torso 26 of the person due to breathing of the lungs of the person and by the random motion of the person. To a much lesser extent, as second sensor 20 is offset from the anatomical location of heart 28 of the person, the reflected second signal is also modulated by the movement of heart 28 of the person.

A portion of the reflected second signal reflects towards second sensor 20. This portion of the reflected second signal is a second reflected signal wirelessly received by second sensor 20. As such, the second reflected signal is of the second signal reflected from the person as modulated by the breathing movement and the random motion of the person. The second reflected signal thereby includes the component corresponding to the breathing movement and the component corresponding to the random motion of the person. The second reflected signal may also contain a component corresponding to the heart movement. Such component is much less in magnitude than the component of the first reflected signal corresponding to the heart movement. Controller 24 communicates with second sensor 20 to receive the second reflected signal.

More descriptively, the component of the second reflected signal (received by second sensor 20) corresponding to the random motion of the person is of similar characteristics as the component of the first reflected signal (received by first or biased sensor 18) corresponding to the random motion of the person. The component of the second reflected signal corresponding to the heart movement is of similar characteristic but is of much less magnitude than the component of the first reflected signal corresponding to the heart movement. As such, the first and second reflected signals include the same component corresponding to the random motion and include unequal components corresponding to the heart movement (i.e., unequal components corresponding to physiological heart activity).

Controller 24 processes the first and second reflected signals to generate a biometric signal indicative of cardiac information of the person sitting in seat 12. Particularly, controller 24 removes the second reflected signal from the first reflected signal to generate a biometric signal having the component corresponding to the movement of heart 28 of the person and being void of the component corresponding to the random motion of the person whereby the biometric signal is indicative of cardiac information of the person.

For instance, the first reflected signal includes a component $c_1HR$ corresponding to the heart movement, a component $BR$ corresponding to the breathing movement, and a component $RM$ corresponding to the random motion of the person. The second reflected signal includes a component $c_2HR$ corresponding to the heart movement, the component $BR$ corresponding to the breathing movement, and the component RM corresponding to the random motion of the person. As indicated, $c_1 \gg c_2$ and therefore the component $c_2$HR of the second reflected signal can be ignored. Controller 24 subtracting the second reflected signal $S_2$ from the first reflected signal $S_1$ isolates the component $c_1$HR corresponding to the heart movement of the first reflected signal (i.e., $S_1-S_2=(c_1\text{HR}+\text{BR}+\text{RM})-(\text{BR}+\text{RM})=c_1\text{HR}$). Controller 24 amplifies and perhaps filters the component $c_1$HR to generate therefrom the biometric signal indicative of cardiac information of the person.

Furthermore, the components BR of the first and second reflected signals S1 and S2 corresponding to the breathing movement may be different from one another as first and second sensors 18 and 20 are positioned differently with respect to one another relative to first and second lungs of the person. That is, the first and second reflected signals S1 and S2 may further include unequal components corresponding to the breathing movement (i.e., unequal components corresponding to physiological respiratory activity). As such, the first reflected signal S1 may include the component $d_1$BR and the second reflected signal S2 may include the component $d_2$BR, where $d_1 \neq d_2$. In this case, controller 24 subtracting the second reflected signal S2 from the first reflected signal S1 further provides the output $d_3$BR where ($d_3$=the magnitude of ($d_2-d_1$)). In turn, controller 24 amplifies and perhaps filters the component $d_3$BR to generate therefrom the biometric signal further indicative of respiratory information of the person.

Figure 3:
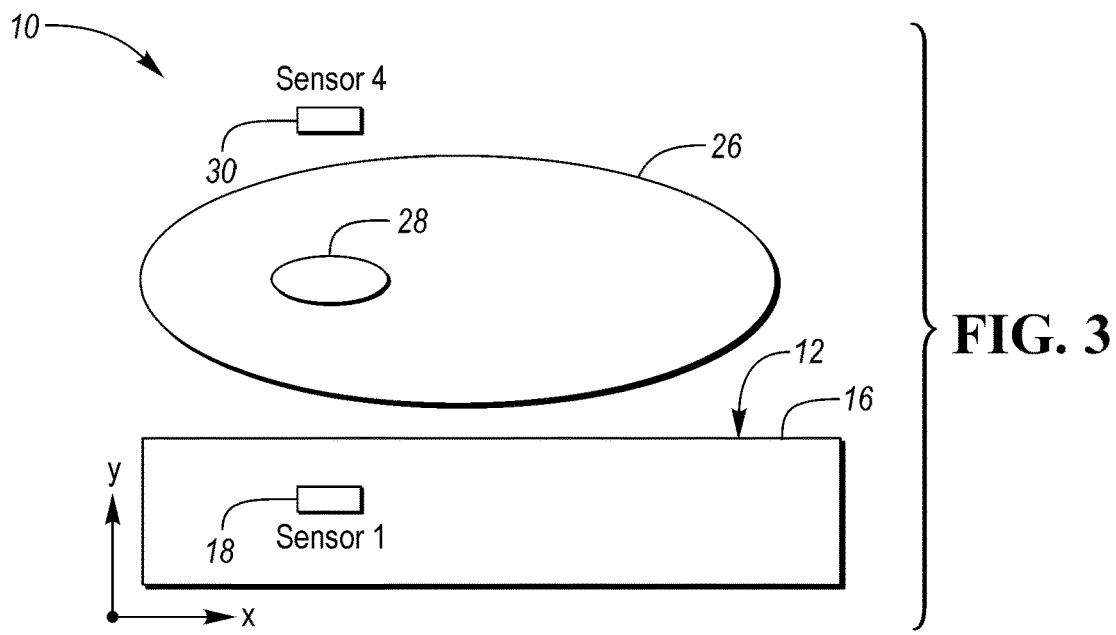
FIG. 3 illustrates a schematic diagram of the seating system according to a second embodiment.

Referring now to FIG. 3, with continual reference to FIG. 1, a schematic diagram of seating system 10 according to a second embodiment is shown. Seating system 10 according to the second embodiment includes first sensor 18 and a fourth Doppler radar sensor ("fourth sensor") 30. As described, first sensor 18 is positioned behind the person within seatback 16 and is aligned with the anatomical location of heart 28 of the person. Fourth sensor 30 is positioned in front of the person at a location within the vehicle and is also aligned with the anatomical location of heart 28 of the person. For instance, fourth sensor 30 is positioned within the instrument panel, the steering wheel, the headliner, etc. of the vehicle to be positioned in front of the person and aligned with the anatomical location of heart 28 of the person.

The schematic diagram shown in FIG. 3 is a sectional view of the x-y plane containing first sensor 18 and fourth sensor 30. Torso 26 of the person sitting in seat 12 and the heart 28 of the person are illustrated per the sectional view.

In operation, controller 24 controls first sensor 18 to wirelessly transmit the first signal from behind the person toward the anatomical location of heart 28 of the person. The first signal reflects from the person and is modulated by the heart movement, the breathing movement, and the random motion of the person. First sensor 18 wirelessly receives the first reflected signal which contains the components corresponding to the heart movement, the breathing movement, and the random motion of the person, respectively. Controller 24 communicates with first sensor 18 to receive the first reflected signal.

Controller 24 controls fourth sensor 30 to wirelessly transmit a fourth signal from in front of the person toward the anatomical location of the person offset from heart 28 of the person. The fourth signal reflects from the person and is modulated by the heart movement, the breathing movement, and the random motion of the person.

As noted, the random motion of the person includes movement of torso 26 of the person caused by the person's body unintentionally moving and bouncing around in seat 12 due to vehicle operation. The effect of the modulation of a reflected signal caused by the random motion relative to first sensor 18 is opposite to the effect of the modulation of a reflected signal caused by the random motion relative to fourth sensor 30. The effects are opposite because first sensor 18 is positioned behind the person, fourth sensor 30 is positioned in front of the person, and first sensor 18 and fourth sensor 30 are aligned with one another. Consequently, the component (e.g., RM) of the first reflected signal corresponding to the random motion of the person relative to the location of first sensor 18 and a component (e.g., -RM) of a reflected signal corresponding to the random motion of the person relative to the location of fourth sensor 30 are additive inverses of one another.

A portion of the reflected fourth signal reflects towards fourth sensor 30. This portion of the reflected fourth signal is a fourth reflected signal wirelessly received by fourth sensor 30. As such, the fourth reflected signal is of the fourth signal reflected from the person as modulated by the heart movement and the breathing movement of the person and by the random motion of the person relative to the location of fourth sensor 30. The fourth reflected signal thereby includes the components corresponding to the heart movement and breathing movement and a component corresponding to the random motion of the person relative to the location of fourth sensor 30. Controller 24 communicates with fourth sensor 30 to receive the fourth reflected signal.

Controller 24 processes the first and fourth reflected signals to generate a biometric signal indicative of cardiac information of the person sitting in seat 12. Particularly, controller 24 adds the first and fourth reflected signals to generate an intermediate signal void of the components of the first and fourth reflected signals corresponding the random motion of the person. This processing involves adding (i) the first reflected signal having components (HR, BR, and RM) corresponding to the heart movement, the breathing movement, and the random motion of the person relative to the location of first sensor 18, respectively, and (ii) the fourth reflected signal having components (HR, BR, and -RM) corresponding to the heart movement, the breathing movement, and the random motion of the person relative to the location of fourth sensor 30, respectively. The components (RM, -RM) corresponding to the random motion of the person relative to first sensor 18 and fourth sensor 30 cancel out. The intermediate signal thereby includes two times the components (HR and BR) corresponding to the heart movement and the breathing movement (i.e., the intermediate signal=2HR+2BR).

This processing further involves filtering the intermediate signal to remove the components corresponding to the breathing movement (i.e., filtered intermediate signal=2HR) and amplifying the filtered intermediate signal to generate a biometric signal having the component (HR) corresponding to the heart movement. The biometric signal is void of the components corresponding to the breathing motion and the random motion of the person whereby the biometric signal is indicative of cardiac information of the person.

Figure 4:
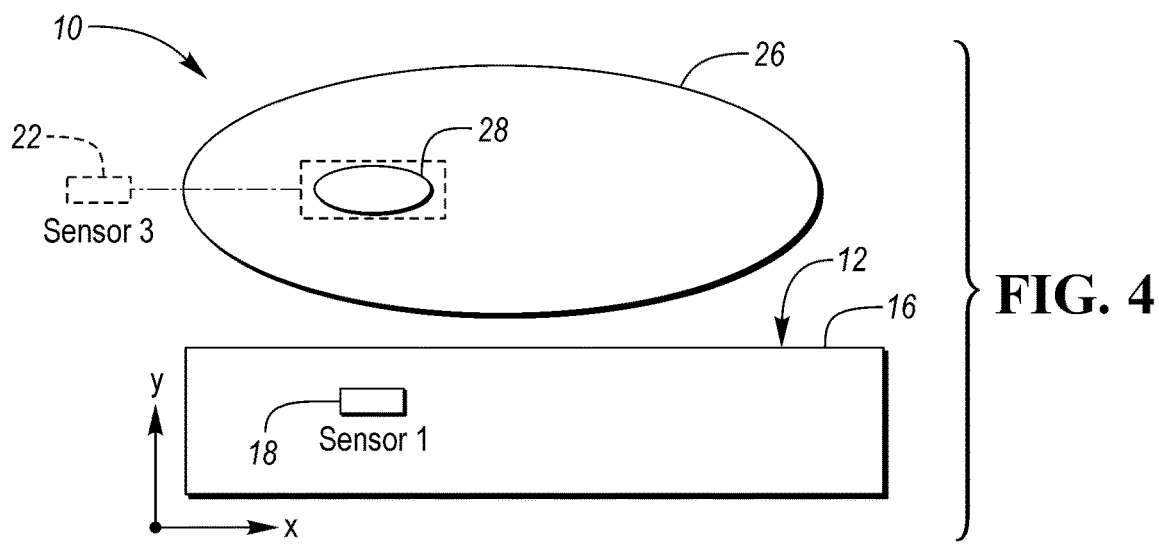
FIG. 4 illustrates a schematic diagram of the seating system according to a third embodiment.

Referring now to FIG. 4, with continual reference to FIG. 1, a schematic diagram of seating system 10 according to a third embodiment is shown. Seating system 10 according to the third embodiment includes first and third sensors 18 and 22. As described with reference to FIG. 1, first sensor 18 is positioned within seatback 16 and is aligned with the anatomical location of heart 28 of the person in a x-y plane; and third sensor 22 is positioned within seat bottom 14 and is aligned with the anatomical location of heart 28 of the person in a y-z plane.

In operation, controller 24 controls first sensor 18 to wirelessly transmit the first signal from behind the person toward the anatomical location of heart 28 of the person. The first signal reflects from the person and is modulated by the heart movement, the breathing movement, and the random motion of the person. A portion of the reflected first signal reflects towards first sensor 18 and is wirelessly received by the first sensor. The first reflected signal includes components corresponding to the heart movement, breathing movement, and random motion of the person relative to the location of first sensor 18. Controller 24 communicates with first sensor 18 to receive the first reflected signal.

Controller controls third sensor 22 to wirelessly transmit the third signal from beneath the person toward the anatomical location of heart 28 of the person. The third signal reflects from the person and is modulated by the heart movement, the breathing movement, and the random motion of the person. A portion of the reflected third signal reflects towards third sensor 22 and is wirelessly received by the third sensor. The third reflected signal includes components corresponding to the heart movement, breathing movement, and random motion of the person relative to the location of third sensor 22. Controller 24 communicates with third sensor 22 to receive the third reflected signal.

The components corresponding to the heart movement, breathing movement, and random motion of the person of the first reflected signal (received by first sensor 18) are different than the components corresponding to the heart movement Controller 24 processes the first and third reflected signals to generate a biometric signal indicative of cardiac information of the person sitting in seat 12. Particularly, controller 24 extracts the component of the first reflected signal corresponding to the heart movement based on a correlation of this component with the component of the third reflected signal corresponding to the heart movement. The extraction is possible as the components of the first and third reflected signals corresponding to the heart movement have similar characteristics whereas the (much larger magnitude) components of the first and third reflected signals corresponding to the random motion of the person have different characteristics as the random motion relative to the location of first sensor 18 in seatback 16 and third sensor 22 in seat bottom 14 is different. Controller 24 generates the biometric signal based on the extracted component of the first reflected signal corresponding to the heart movement. The biometric signal is therefore void of the components corresponding to the breathing movement and the random motion of the person whereby the biometric signal is indicative of cardiac information of the person.

Figure 5:
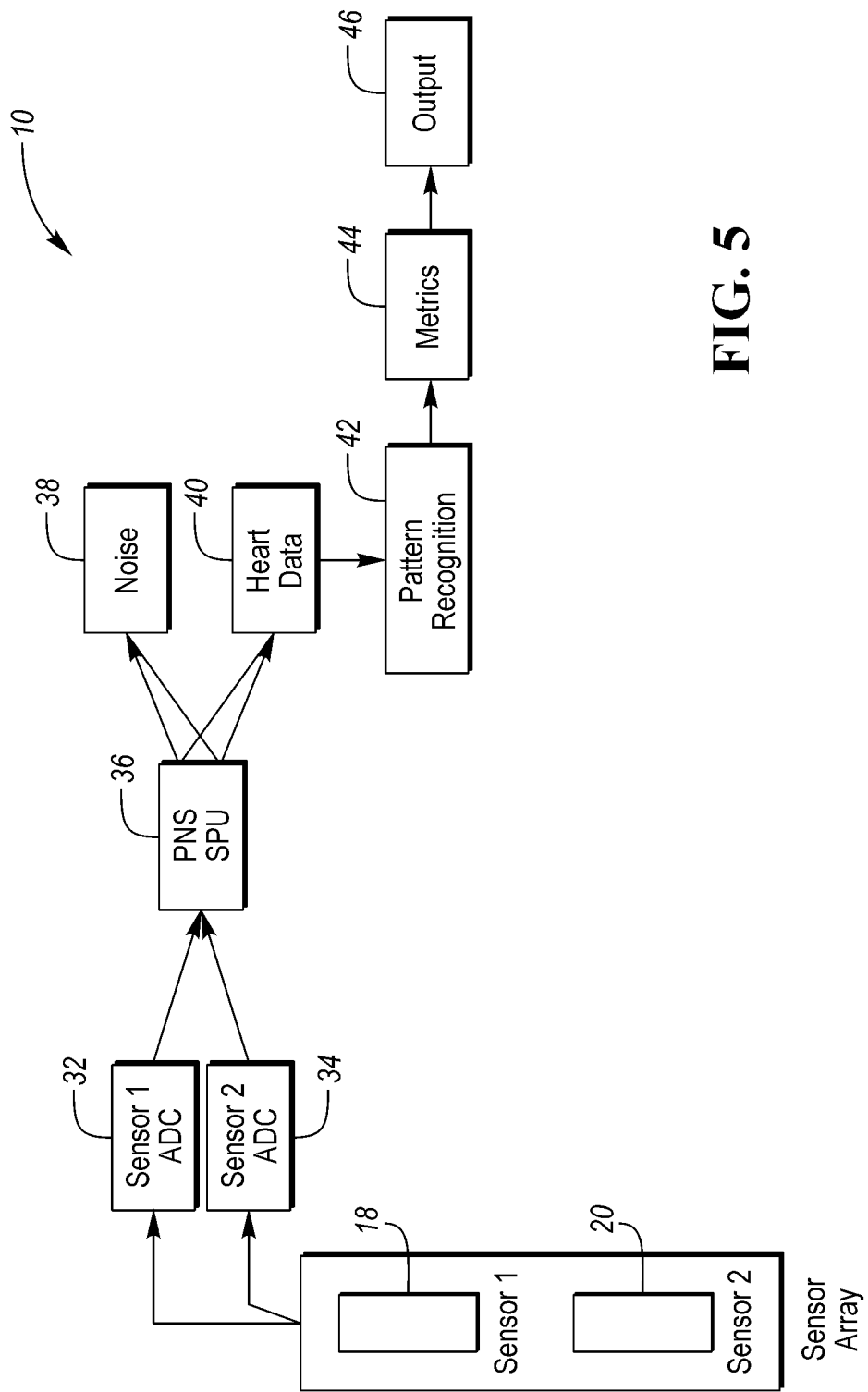
FIG. 5 illustrates a functional block diagram of the seating system according to the first embodiment.

Referring now to FIG. 5, with continual reference to FIGS. 1 and 2, a functional block diagram of seating system 10 is shown. The functional block diagram of seating system 10 is pertinent to all the embodiments of the seating system described herein, but will be described with reference to the first embodiment of the seating system shown in FIG. 2. In general, controller 24 performs the functions of the functional block diagram.

A first ADC (analog-to-digital converter) 32 of controller 24 receives the first reflected signal from first sensor 18. The first reflected signal contains components corresponding to the heart movement, the breathing movement, and the random motion of the person. First ADC 32 converts the received first reflected signal from its analog format into digital format. A second ADC 34 of controller 24 receives the second reflected signal from second sensor 20. The second reflected signal contains components corresponding to the breathing movement and the random motion of the person. The second reflected signal further contains a component corresponding to the heart movement—this component being relatively reduced in comparison with the component of the first reflected signal corresponding to the heart movement. Second ADC 36 converts the received second reflected signal from its analog format into digital format.

First ADC 34 provides a digitized version of the received first reflected signal to SPU (signal processing unit) 36 of controller 24 and second ADC 36 provides a digitized version of the received second reflected signal to the SPU. SPU 36 processes the digitized versions of the reflected signals to remove the components of the second reflected signal from the components of the first reflected signal to thereby generate a biometric signal having the component of the first reflected signal corresponding to the heart movement. As described, the components removed from the first reflected signal are the components corresponding to the breathing movement and the random motion of the person. These removed components are identified as noise 38 in FIG. 5. The resulting biometric signal contains the component of the first reflected signal corresponding to the heart movement and is void of the other components. The resulting biometric signal is therefore indicative of cardiac information of the person and is identified by heart data 40 in FIG. 5.

Controller 24 analyzes the biometric signal for various pattern recognition analysis as indicated by functional block 42. For instance, controller 24 analyzes the biometric signal using pattern recognition analysis to extract various vital criteria including heart rate, heart rate variability, etc. Controller 24 generates metrics based on the results of the pattern recognition analysis as indicated by functional block 44 and outputs the results as indicated by functional block 46.

Figure 6:
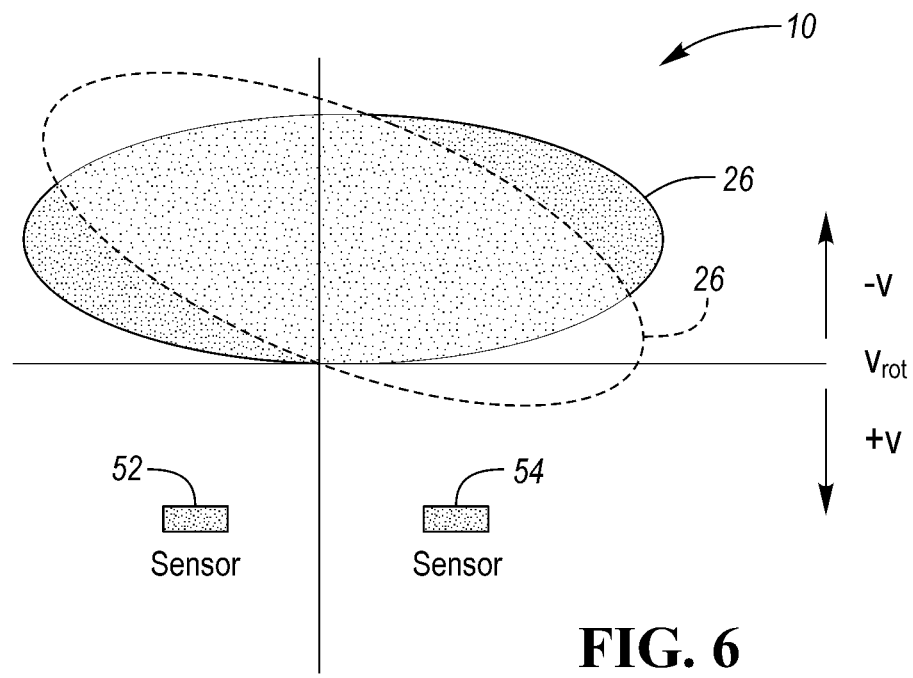
FIG. 6 illustrates a schematic diagram of the seating system according to a fourth embodiment.

Referring now to FIG. 6, with continual reference to FIG. 1, a schematic diagram of seating system 10 according to a fourth embodiment is shown. Seating system 10 according to the fourth embodiment includes a fifth Doppler radar sensor ("fifth sensor") 50 and a sixth Doppler radar sensor ("sixth sensor") 52. Fifth and sixth sensors 50 and 52 are positioned at respective locations within seatback 16 and are in the same x-y plane. Fifth sensor 50 is aligned with an anatomical location on the left side of torso 26 of the person sitting in seat 12. Sixth sensor 52 is aligned with an anatomical location on the right side of torso 26 of the person sitting in seat 12. Although not necessary, sensors 50 and 52 are geometrically reflected about a center axis 54. The schematic diagram shown in FIG. 6 is a sectional view of the x-y plane containing sensors 50 and 52.

In operation, controller 24 controls fifth sensor 50 to wirelessly transmit a fifth signal from behind the person toward the left side of torso 26. The fifth signal reflects from the left side of torso 26 and is modulated by rotation movement of torso 26 from the person moving and shifting position in seat 12. Fifth sensor 50 wirelessly receives the fifth reflected signal which contains a component corresponding to the torso rotation movement relative to the location of the fifth sensor. Controller 24 communicates with fifth sensor 50 to receive the fifth reflected signal.

Controller 24 controls sixth sensor 52 to wirelessly transmit a sixth signal from behind the person toward the right side of torso 26. The sixth signal reflects from the right side of torso 26 and is modulated by the rotation movement of torso 26. Sixth sensor 52 wirelessly receives the sixth reflected signal which contains a component corresponding to the torso rotation movement relative to the location of the sixth sensor. Controller 24 communicates with sixth sensor 50 to receive the sixth reflected signal.

The effect of the modulation of a reflected signal caused by the torso rotation movement of torso 26 relative to fifth sensor 50 is opposite to the effect of the modulation of a reflected signal caused by the torso rotation movement relative to sixth sensor 30. The effects are opposite because fifth sensor 50 is aligned with an anatomical location on the left side of torso 26, sixth sensor 52 is aligned with an anatomical location on the right side of torso 26, and sensors 50 and 52 are geometrically reflected about center axis 54.

Controller 24 compares fifth and sixth reflected signals to generate a position signal indicative of positioning information of the person sitting in seat 12. Particularly, using pulsed or sourced frequency modulated CW (continuous wave) radar with multisource antennas (i.e., fifth and sixth sensors 50 and 52) allows for position information to be decoded from the reflected signals. Velocity and position can be deciphered where the inverse properties of the rotation impact regarding sensors 50 and 52 can help to identify and quantify the rotation of the person (or some other object) sitting in seat 12. This can be used to determine non-random motion and occupant out-of-position coordinates. Additionally, this information can help to remove rotational corruption in a biometric signal to better resolve the heart function. Further, coupling with pure CW radar the position invariance aspect can allow for precise differentiation between vital sign inputs and non-vital signal inputs like rotation.

Figure 7:
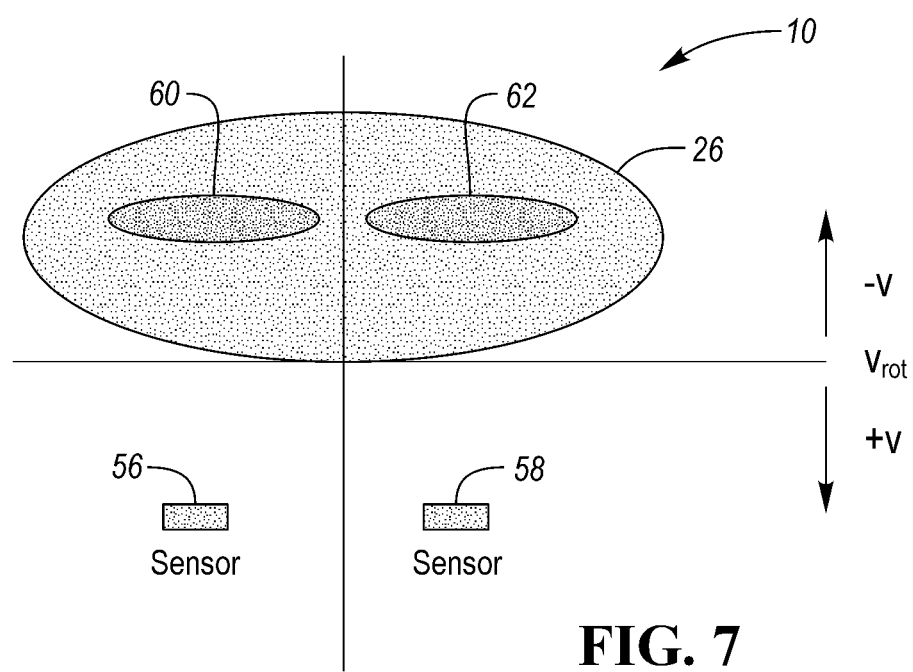
FIG. 7 illustrates a schematic diagram of the seating system according to a fifth embodiment.

Referring now to FIG. 7, with continual reference to FIG. 1, a schematic diagram of seating system 10 according to a fifth embodiment is shown. Seating system 10 according to the fourth embodiment includes a seventh Doppler radar sensor ("seventh sensor") 56 and an eighth Doppler radar sensor ("eighth sensor") 58. Seventh and eighth sensors 56 and 58 are positioned at respective locations within seatback 16 and are in the same x-y plane. Seventh sensor 56 is aligned with an anatomical location of a left lung 60 of a person sitting in seat 12. Eighth sensor 58 is aligned with an anatomical location of a right lung 62 of the person sitting in seat 12.

In operation, controller 24 controls seventh sensor 56 to wirelessly transmit a seventh signal from behind the person toward left lung 60 of the person. The seventh signal reflects from left lung 60 and is modulated by breathing movement of the left lung. Seventh sensor 56 wirelessly receives the seventh reflected signal which contains a component corresponding to breathing movement of left lung 60. Controller 24 communicates with seventh sensor 56 to receive the seventh reflected signal.

Controller 24 controls eighth sensor 58 to wirelessly transmit an eighth signal from behind the person toward right lung 62 of the person. The eighth signal reflects from right lung 62 and is modulated by breathing movement of the right lung. Eighth sensor 58 wirelessly receives the eighth reflected signal which contains a component corresponding to the breathing movement of right lung 62. Controller 24 communicates with eighth sensor 58 to receive the eighth reflected signal.

Controller 24 compares seventh and eighth reflected signals to generate a lung status signal indicative of respiratory information of the person sitting in seat 12. Particularly, the assumption that lungs 60 and 62 will function relatively uniformly laterally is used in the normative case. However, injury or respiratory illness can create lateral variation which can be used for diagnostics.

As described, embodiments of the present invention may involve Doppler sensor fusion that is based upon separation of variables. The similarities and differences in two sensors are used to extract a desired signal such as the heartbeat. A relatively simple point-of-care (POC) algorithm involving the mechanical displacement spatiotemporal relationship between thoracic non-physiological motion and heart and respiratory function is utilized. While total thoracic motion occurs primarily in a rigid systematic manner it is hypothesized that the subcomponents exhibit a lateral bias in time and space. These spatial biases being the result of the lung differences (two lobes versus three lobes) for respiration and the anatomical location and dampening differences for the heart. The temporal biases form the difference in sensor spatial locations. These differences can be exploited to extract heart and lung function when lateral Doppler sensor arrays are employed. In cases where neither sensor is optimally located in relation to the person, pattern recognition and machine learning may overcome this issue.

A basic concept of the POC algorithm works under the assumption that the mechanical noise due to vibration is relatively uniform in space while the physiological mechanics are not. Just as the eyes and ears triangulate the position of a specific object or sound in space, dual radar sensors allow the same. For the POC algorithm, a simple deconvolution, which can be interpreted in rudimentary terms as dividing one signal by the other in their frequency domains, is performed. If the assumption is correct that the noise is uniform, then dividing one by the other is the same as dividing something by itself yielding a value of one. However, for physiological assumptions the nonuniformity means that dividing the stronger signal by the weaker signal yields a value greater than one for that signal component. Nothing in the signal is cut out (i.e., no filtering is applied), but rather the signal differences are exaggerated. If the hypothesis is correct, then those signal differences are primarily physiological by nature even when the noise signal is larger than the target signal (as will usually be the case).

In cases where the heart signal is much weaker than the noise even after fusion, the targets can still be extracted. This is because sub-features are revealed during fusion allowing for pattern recognition. Machine learning may also be used to find the heart beats within the signal. As described herein, whether the sensors are optimally placed for that person's anatomy or not, the combination of sensor fusion with pattern recognition and machine learning allows accurate heart activity information (heart rate, heart rate variability, etc.) to be extracted.

While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. A seating system for a vehicle comprising:
   a vehicle seat with a seatback;
   a first sensor positioned at a first location within the seatback corresponding to an anatomical location of a heart of a person sitting in the seat, the first sensor is configured to transmit a first signal from behind the person toward the anatomical location of the heart and to receive a first reflected signal of the first signal reflected from the person as modulated by movement of the heart and by a random motion of the person, wherein the first reflected signal includes a component corresponding to the movement of the heart and a component corresponding to the random motion of the person;
a second sensor positioned at a second location within the seatback corresponding to an anatomical location of the person offset from the heart, the second sensor is configured to transmit a second signal from behind the person toward the anatomical location of the person offset from the heart and to receive a second reflected signal of the second signal reflected from the person as modulated by the random motion of the person, wherein the second reflected signal includes the component corresponding to the random motion of the person; and
a controller configured to remove the second reflected signal from the first reflected signal to generate a biometric signal having the component corresponding to the movement of the heart and being void of the component corresponding to the random motion of the person whereby the biometric signal is indicative of cardiac information of the person.

2. The seating system of claim 1 wherein:
the first location of the first sensor, the second location of the second sensor, and the anatomical location of the heart are in a common plane.

3. The seating system of claim 1 wherein:
the vehicle seat further includes a seat bottom;
the seating system further includes a third sensor positioned at a third location within the seat bottom corresponding to the anatomical location of the heart, the third sensor is configured to transmit a third signal from beneath the person toward the anatomical location of the heart and to receive a third reflected signal of the third signal reflected from the person as modulated by the movement of the heart relative to the third location of the third sensor, wherein the third reflected signal includes a component corresponding to the movement of the heart relative to the third location of the third sensor; and
the controller is further configured to process the first and third reflected signals to extract from the first reflected signal the component corresponding to the movement of the heart based on a correlation with the component of the third reflected signal corresponding to the movement of the heart relative to the location of the third sensor and to generate a second biometric signal having the extracted component of the first reflected signal corresponding to the movement of the heart whereby the biometric signal is indicative of cardiac information of the person.

4. The seating system of claim 3 wherein:
the location of the first sensor, the location of the third sensor, and the anatomical location of the heart are in a common plane orthogonal to the common plane of the location of the first sensor, the location of the second sensor, and the anatomical location of the heart.

5. The seating system of claim 1 further comprising:
a third sensor positioned at a third location within the seatback corresponding to an anatomical location of a left side of a torso of the person, the third sensor is configured to transmit a third signal from behind the person toward the anatomical location of the left side of the torso and to receive a third reflected signal of the third signal reflected from the person as modulated by rotation movement of the torso, wherein the third reflected signal includes a component corresponding to the rotation movement of the torso relative to the third location of the third sensor;
a fourth sensor positioned at a fourth location within the seatback corresponding to an anatomical location of a right side of the torso, the fourth sensor is configured to transmit a fourth signal from behind the person toward the anatomical location of the right side of the torso and to receive a fourth reflected signal of the fourth signal reflected from the person as modulated by rotation movement of the torso, wherein the fourth reflected signal includes a component corresponding to the rotation movement of the torso relative to the fourth location of the fourth sensor; and
wherein the controller is further configured to generate a position signal indicative of positioning information of the person based on a comparison of the third and fourth reflected signals.

6. The seating system of claim 1 further comprising:
a third sensor positioned at a third location within the seatback corresponding to an anatomical location of a left lung of the person, the third sensor is configured to transmit a third signal from behind the person toward the anatomical location of the left lung and to receive a third reflected signal of the third signal reflected from the person as modulated by movement of the left lung, wherein the third reflected signal includes a component corresponding to the movement of the left lung;
a fourth sensor positioned at a fourth location within the seatback corresponding to an anatomical location of a right lung of the person, the fourth sensor is configured to transmit a fourth signal from behind the person toward the anatomical location of the right lung and to receive a fourth reflected signal of the fourth signal reflected from the person as modulated by movement of the right lung, wherein the fourth reflected signal includes a component corresponding to the movement of the right lung; and
wherein the controller is further configured to generate a lung status signal indicative of respiratory information of the person based on a comparison of the third and fourth reflected signals.

7. The seating system of claim 1 wherein:
the first sensor is a first Doppler radar sensor and the second sensor is a second Doppler radar sensor.

8. A seating system for a vehicle comprising:
a vehicle seat with a seatback;
a first sensor positioned at a first location within the seatback corresponding to an anatomical location of a heart of a person sitting in the seat, the first sensor is configured to transmit a first signal from behind the person toward the anatomical location of the heart and to receive a first reflected signal of the first signal reflected from the person as modulated by a movement of the heart and by a random motion of the person relative to the location of the first sensor, wherein the first reflected signal includes a component corresponding to the movement of the heart and a component corresponding to the random motion of the person relative to the first location of the first sensor;
a second sensor positioned in front of the person at a second location within the vehicle corresponding to the anatomical location of the heart, the second sensor is configured to transmit a second signal from in front of the person toward the anatomical location of the heart and to receive a second reflected signal of the second signal reflected from the person as modulated by the movement of the heart and by the random motion of the person relative to the location of the second sensor, wherein the second reflected signal includes the component corresponding to the movement of the heart and a component corresponding to the random motion of the person relative to the second location of the second sensor;

wherein the component of the first reflected signal corresponding to the random motion of the person relative to the first location of the first sensor and the component of the second reflected signal corresponding to the random motion of the person relative to the second location of the second sensor are additive inverses of one another; and a controller configured to combine the first and second reflected signals to generate a biometric signal having the component corresponding to the movement of the heart and being void of the components corresponding to the random motion of the person relative to the locations of the first and second sensors whereby the biometric signal is indicative of cardiac information of the person.

9. The seating system of claim 8 wherein:
the first location of the first sensor, the second location of the second sensor, and the anatomical location of the heart are in a common plane.

10. The seating system of claim 8 further comprising:
a third sensor positioned at a third location within the seatback corresponding to an anatomical location of a left side of a torso of the person, the third sensor is configured to transmit a third signal from behind the person toward the anatomical location of the left side of the torso and to receive a third reflected signal of the third signal reflected from the person as modulated by rotation movement of the torso, wherein the third reflected signal includes a component corresponding to the rotation movement of the torso relative to the third location of the third sensor;
a fourth sensor positioned at a fourth location within the seatback corresponding to an anatomical location of a right side of the torso, the fourth sensor is configured to transmit a fourth signal from behind the person toward the anatomical location of the right side of the torso and to receive a fourth reflected signal of the fourth signal reflected from the person as modulated by rotation movement of the torso, wherein the fourth reflected signal includes a component corresponding to the rotation movement of the torso relative to the fourth location of the fourth sensor; and
wherein the controller is further configured to generate a position signal indicative of positioning information of the person based on a comparison of the third and fourth reflected signals.

11. The seating system of claim 8 further comprising:
a third sensor positioned at a third location within the seatback corresponding to an anatomical location of a left lung of the person, the third sensor is configured to transmit a third signal from behind the person toward the anatomical location of the left lung and to receive a third reflected signal of the third signal reflected from the person as modulated by movement of the left lung, wherein the third reflected signal includes a component corresponding to the movement of the left lung;
a fourth sensor positioned at a fourth location within the seatback corresponding to an anatomical location of a right lung of the person, the fourth sensor is configured to transmit a fourth signal from behind the person toward the anatomical location of the right lung and to receive a fourth reflected signal of the fourth signal reflected from the person as modulated by movement of the right lung, wherein the fourth reflected signal includes a component corresponding to the movement of the right lung; and
wherein the controller is further configured to generate a lung status signal indicative of respiratory information of the person based on a comparison of the third and fourth reflected signals.

12. The seating system of claim 8 wherein:
the first sensor is a first Doppler radar sensor and the second sensor is a second Doppler radar sensor.

13. A seating system for a vehicle comprising:
a vehicle seat with a seatback and a seat bottom;
a first sensor positioned at a first location within the seatback corresponding to an anatomical location of a heart of a person sitting in the seat, the first sensor is configured to transmit a first signal from behind the person toward the anatomical location of the heart and to receive a first reflected signal of the first signal reflected from the person as modulated by a movement of the heart relative to the first location of the first sensor, wherein the first reflected signal includes a first component corresponding to the movement of the heart relative to the first location of the first sensor;
a second sensor positioned at a second location within the seat bottom corresponding to the anatomical location of the heart, the second sensor is configured to transmit a second signal from beneath the person toward the anatomical location of the heart and to receive a second reflected signal of the second signal reflected from the person as modulated by the movement of the heart relative to the second location of the second sensor, wherein the second reflected signal includes a second component corresponding to the movement of the heart relative to the second location of the second sensor; and
a controller configured to process the first and second reflected signals to extract the first component from the first reflected signal based on a correlation with the second component of the second reflected signal and to generate a biometric signal having the first component whereby the biometric signal is indicative of cardiac information of the person.

14. The seating system of claim 13 wherein:
the first location of the first sensor, the second location of the second sensor, and the anatomical location of the heart are in a common plane.

15. The seating system of claim 13 further comprising:
a third sensor positioned at a third location within the seatback corresponding to an anatomical location of a left side of a torso of the person, the third sensor is configured to transmit a third signal from behind the person toward the anatomical location of the left side of the torso and to receive a third reflected signal of the third signal reflected from the person as modulated by rotation movement of the torso, wherein the third reflected signal includes a component corresponding to the rotation movement of the torso relative to the third location of the third sensor;
a fourth sensor positioned at a fourth location within the seatback corresponding to an anatomical location of a right side of the torso, the fourth sensor is configured to transmit a fourth signal from behind the person toward the anatomical location of the right side of the torso and to receive a fourth reflected signal of the fourth signal reflected from the person as modulated by rotation movement of the torso, wherein the fourth reflected signal includes a component corresponding to the rotation movement of the torso relative to the fourth location of the fourth sensor; and wherein the controller is further configured to generate a position signal indicative of positioning information of the person based on a comparison of the third and fourth reflected signals.

16. The seating system of claim 13 wherein:

the first sensor is a first Doppler radar sensor and the second sensor is a second Doppler radar sensor.

* * * * *